US00PP22614P2

(12) United States Plant Patent
Possemiers

(10) Patent No.: US PP22,614 P2
(45) Date of Patent: Apr. 3, 2012

(54) ***HYDRANGEA* PLANT NAMED 'LEVANA'**

(50) Latin Name: *Hydrangea paniculata*
Varietal Denomination: Levana

(76) Inventor: Johan Possemiers, Brecht (BE)

( * ) Notice: Subject to any disclaimer, the term of this patent is extended or adjusted under 35 U.S.C. 154(b) by 0 days.

(21) Appl. No.: 12/925,595

(22) Filed: Oct. 25, 2010

(51) Int. Cl.
*A01H 5/00* (2006.01)

(52) U.S. Cl. ..... Plt./250
(58) Field of Classification Search ..... Plt./250
See application file for complete search history.

*Primary Examiner* — Annette Para
(74) *Attorney, Agent, or Firm* — C. A. Whealy

(57) ABSTRACT

A new and distinct cultivar of *Hydrangea* plant named 'Levana', characterized by its upright plant habit; strong and sturdy stems that hold inflorescences upright; large lacecap-type inflorescences with large white-colored sterile flowers; and fragrant flowers are attractive to butterflies, particularly *Araschnia levana.*

2 Drawing Sheets

Botanical designation: *Hydrangea paniculata.*
Cultivar denomination: 'LEVANA'.

BACKGROUND OF THE INVENTION

The present invention relates to a new and distinct cultivar of *Hydrangea* plant, botanically known as *Hydrangea paniculata* and hereinafter referred to by the name 'Levana'.

The new *Hydrangea* plant is a product of a planned breeding program conducted by the Inventor in Brecht, Belgium. The objective of the breeding program was to develop new *Hydrangea* plants with strong stems, reliability and tolerant to pathogens and pests.

The new *Hydrangea* plant originated from an open-pollination in 1996 of *Hydrangea paniculata* 'Barbara', disclosed in U.S. Plant Pat. No. 13,606, as the female, or seed parent and an unknown selection of *Hydrangea paniculata* as the male, or pollen, parent. The new *Hydrangea* plant was discovered and selected by the Inventor in 2002 as a flowering plant within the progeny of the stated open-pollination in a controlled environment in Brecht, Belgium.

Asexual reproduction of the new cultivar by softwood cuttings in a controlled environment in Brecht, Belgium has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment such as temperature and light intensity without, however, any variance in genotype.

The following traits have been repeatedly observed and are determined to be the unique characteristics of 'Levana'. These characteristics in combination distinguish 'Levana' as a new and distinct cultivar of *Hydrangea* plant:

1. Upright plant habit.
2. Strong and sturdy stems that hold inflorescences upright.
3. Large lacecap-type inflorescences with large white-colored sterile flowers.

4. Fragrant flowers are attractive to butterflies, particularly *Araschnia levana.*

Plants of the new *Hydrangea* differ from plants of the female parent, 'Barbara', in the following characteristics:

1. Plants of the new *Hydrangea* have stronger stems than plants of 'Barbara'.
2. Plants of the new *Hydrangea* have larger and more uniform inflorescences than plants of 'Barbara'.
3. Sterile flowers of plants of the new *Hydrangea* have smaller sepals than sterile flowers of plants of 'Barbara'.

Plants of the new *Hydrangea* can be compared to plants of *Hydrangea paniculata* 'Le Vasterival', disclosed in U.S. Plant Pat. No. 20,272. In side-by-side comparisons, plants of the new *Hydrangea* differ from plants of 'Le Vasterival' in the following characteristics:

1. Plants of the new *Hydrangea* are more upright than plants of 'Le Vasterival'.
2. Plants of the new *Hydrangea* have stronger stems than plants of 'Le Vasterival'.
3. Plants of the new *Hydrangea* have larger inflorescences than plants of 'Le Vasterival'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Levana' grown in a container.

The photograph at the top of the second sheet is a close-up view of a typical inflorescence of 'Levana'.

The photograph at the bottom of the second sheet is a close-up view of typical leaves of 'Levana'.

DETAILED BOTANICAL DESCRIPTION

Plants used for the aforementioned photographs and the following description were grown during the autumn in an outdoor nursery in The Netherlands and under conditions which closely approximate commercial *Hydrangea* production conditions. During the production of the plants, day temperatures ranged from 13° C. to 25° C. and night temperatures ranged from 4° C. to 16° C. Plants of the new *Hydrangea* were 18 months old when the photographs and description were taken. In the following description, color references are made to The Royal Horticultural Society Colour Chart, 2007 Edition, except where general terms of ordinary dictionary significance are used.

Botanical description: *Hydrangea paniculata* 'Levana'.

Parentage:

*Female, or seed, parent.*—*Hydrangea paniculata* 'Barbara', disclosed in U.S. Plant Pat. No. 13,606.

*Male, or pollen, parent.*—Unknown selection of *Hydrangea paniculata*, not patented.

Propagation:

*Type cutting.*—By softwood cuttings.

*Time to produce a rooted young plant, summer.*—About one month at temperatures of about 30° C. to 35° C.

*Time to produce a rooted young plant, winter.*—About two to three months at temperatures of about 5° C. to 10° C.

*Root description.*—Medium in thickness, fleshy; light brown to white in color.

*Rooting habit.*—Moderate branching; medium in density.

Plant description:

*Plant form and growth habit.*—Perennial deciduous shrub; upright plant habit; broadly inverted triangle; strong and sturdy lateral branches; moderately vigorous growth habit.

*Plant height.*—About 64.5 cm.

*Plant diameter or area of spread.*—About 64.4 cm.

*Lateral branches.*—Length: About 34.3 cm. Diameter: About 4 mm. Internode length: About 6.1 cm. Texture, developing: Sparsely pubescent. Texture, developed: Smooth, glabrous. Strength: Strong, sturdy. Color, developing: Close to 146C. Color, developed: Close to 199A.

Foliage description:

*Arrangement.*—Opposite, simple.

*Length.*—About 13.5 cm.

*Width.*—About 7.2 cm.

*Shape.*—Ovate to elliptic.

*Apex.*—Short apiculate.

*Base.*—Rounded to short attenuate.

*Margin.*—Serrate.

*Texture, upper and lower surfaces.*—Pubescent.

*Venation pattern.*—Pinnate.

*Color.*—Developing leaves, upper surface: Close to 143A and 144A. Developing leaves, lower surface: Close to 146B. Fully expanded leaves, upper surface: Close to 146A; venation, close to 147C to 147D. Fully expanded leaves, lower surface: Close to 147B to 147C; venation, close to 193B to 193C.

*Petioles.*—Length: About 2.5 cm. Diameter: About 3 mm. Texture, upper and lower surfaces: Pubescent. Color, upper surface: Close to 177A. Color, lower surface: Close to 146C to 146D and 195A.

Flower description:

*Flower type and habit.*—Single sterile and fertile flowers arranged on large terminal and axillary lacecap-type panicles; panicles broadly conical in shape; flowers face upright to outwardly.

*Fragrance.*—Moderately fragrant, sweet; fragrant flowers are attractive to butterflies, particularly *Araschnia levana.*

*Natural flowering season.*—Continuous flowering throughout the summer to early autumn in The Netherlands.

*Flower longevity, fertile flowers.*—Flowers last about one week on the plant; flowers not persistent.

*Flower longevity, sterile flowers.*—Flowers last about three weeks on the plant; flowers persistent.

*Quantity of flowers.*—Freely flowering; about 200 fertile flowers and about 15 sterile flowers per inflorescence.

*Inflorescence height.*—About 17.2 cm.

*Inflorescence diameter.*—About 16.1 cm.

*Flower diameter, fertile flowers.*—About 1 cm.

*Flower depth (height), fertile flowers.*—About 9 mm.

*Flower diameter, sterile flowers.*—About 5.2 cm.

*Flower depth (height), sterile flowers.*—About 9 mm.

*Flower buds, fertile flowers.*—Length: About 4 mm. Diameter: About 3 mm. Shape: Broadly ovoid. Color: Close to 150D.

*Flower buds, sterile flowers.*—Length: About 7 mm. Diameter: About 4 mm. Shape: Obovate. Color: Close to 150D and 157A.

*Petals, fertile flowers only.*—Arrangement: Five in a single whorl. Length: About 4 mm. Width: About 1.5 mm. Shape: Ovate. Apex: Acute. Base: Cuneate. Margin: Entire. Texture, upper and lower surfaces: Smooth, glabrous. Color: When opening, upper and lower surfaces: Close to NN155B. Fully opened, upper and lower surfaces: Close to NN155B.

*Sepals, fertile flowers.*—Quantity per flower: Five in a single whorl. Length: About 1 mm. Width: About 1 mm. Shape: Ovate. Apex: Acute. Base: Broadly cuneate. Margin: Entire. Texture, upper and lower surfaces: Smooth, glabrous. Color, upper and lower surfaces: Close to 157B.

*Sepals, sterile flowers.*—Quantity per flower: About four in a single whorl. Length: About 2.7 cm. Width: About 2.2 cm. Shape: Broadly elliptical to broadly obovate. Apex: Rounded to retuse. Base: Cuneate. Margin: Entire. Texture, upper and lower surfaces: Smooth, glabrous. Color: When opening, upper surface: Close to 157C to 157D. When opening, lower surface: Close to 157D. Fully opened, upper and lower surfaces: Close to 157D and 155A; with development, color becomes closer to 145B.

*Pedicels, fertile flowers.*—Strength: Moderately strong. Length: About 2 mm. Diameter: About 0.5 mm. Texture: Smooth, glabrous. Color: Close to 157C to 157D.

*Pedicels, sterile flowers.*—Strength: Moderately strong. Length: About 2.2 cm. Diameter: About 1 mm. Texture: Smooth, glabrous. Color: Close to N155A to N155B.

*Reproductive organs, fertile flowers only.*—Stamens: Quantity per flower: About ten. Filament length: About 5 mm. Filament color: Close to N155A. Anther shape: Reniform. Anther length: About 1 mm. Anther color: Close to 155A. Pollen amount: Scarce. Pollen color: Close to 158C to 158D. Pistils: Pistil quantity per flower: One. Pistil length: About 1.5 mm. Stigma shape: Two to three-lobed. Stigma color: Close to 155C. Style length: About 1 mm. Style color: Close to 155A to 155B. Ovary color: Close to 155A to 155B.

*Seeds/fruits.*—Seed and fruit development have not been observed on plants of the new *Hydrangea*.

Disease/pest resistance: Plants of the new *Hydrangea* have not been observed to be resistant to pathogens or pests common to *Hydrangea*.

Temperature tolerance: Plants of the new *Hydrangea* have been shown to be hardy to USDA Hardiness Zone 4 and tolerant to high temperatures of about 40° C.

It is claimed:

1. A new and distinct *Hydrangea* plant named 'Levana' as illustrated and described.

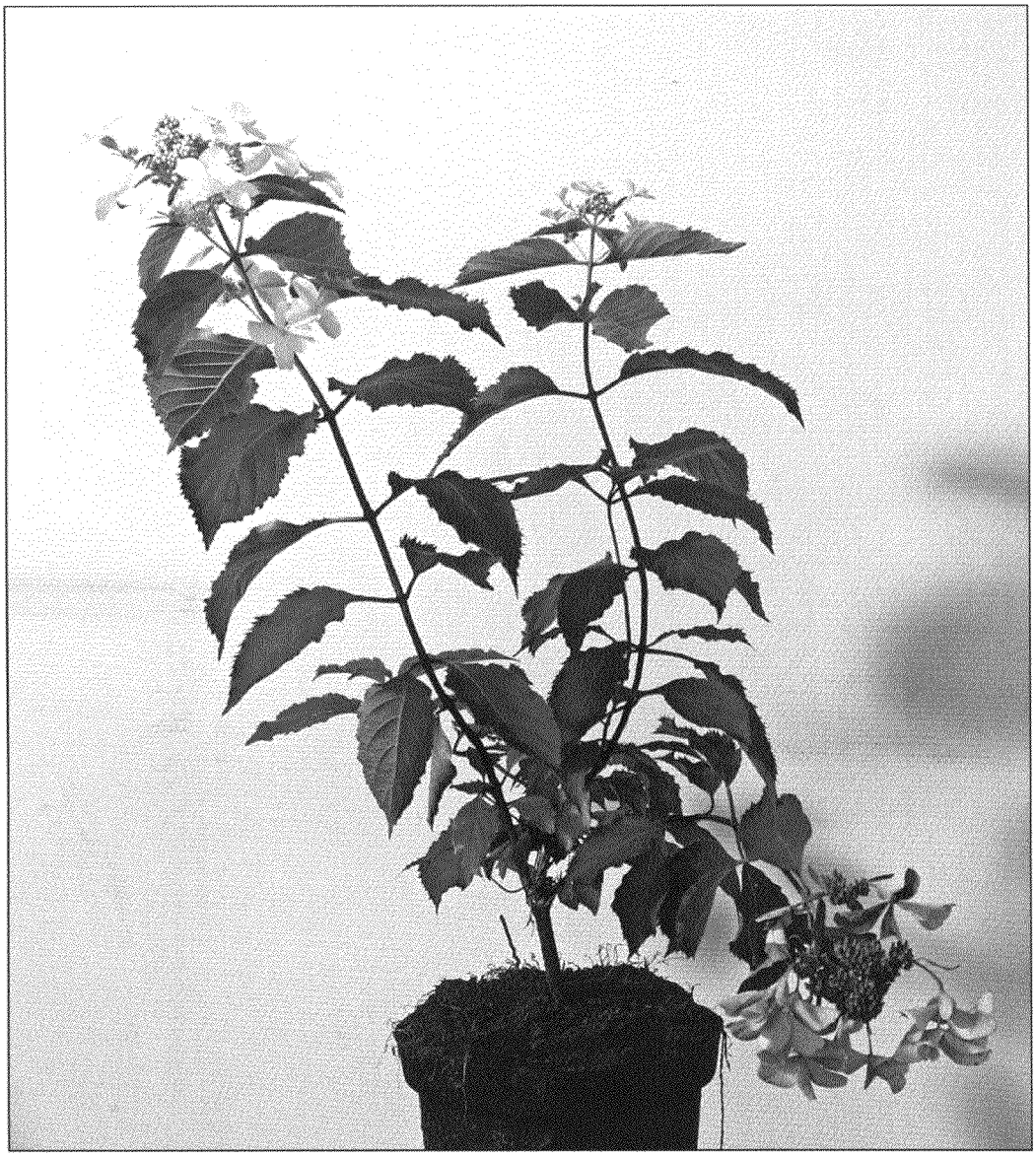

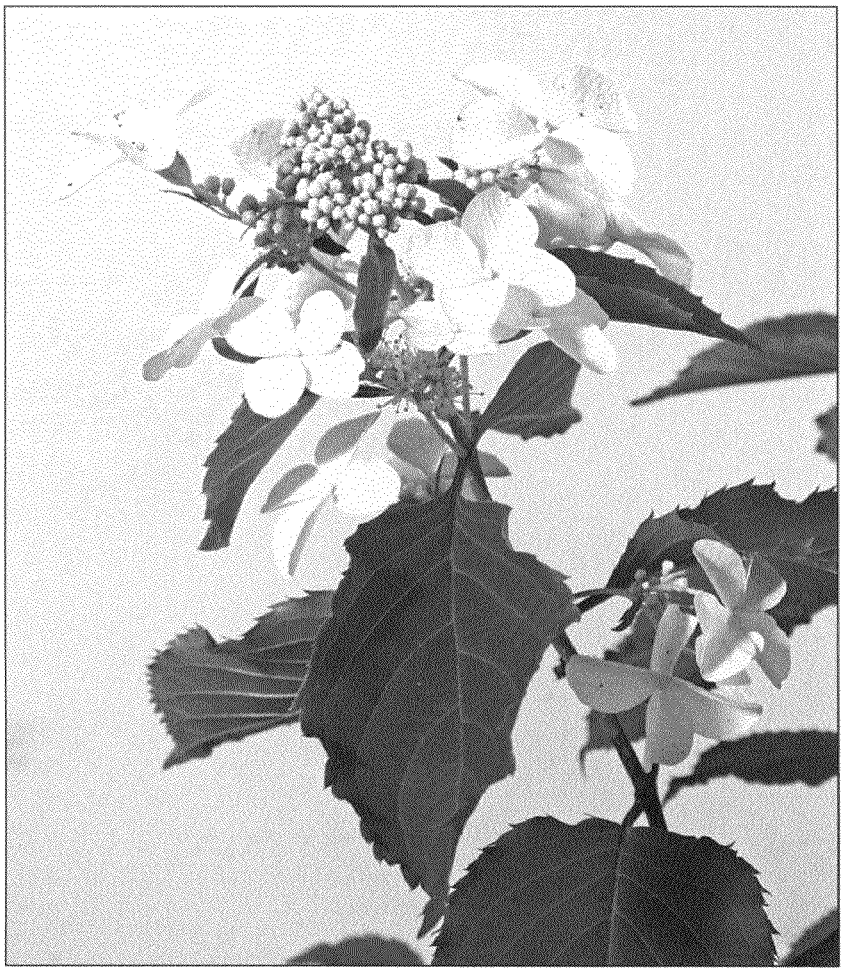
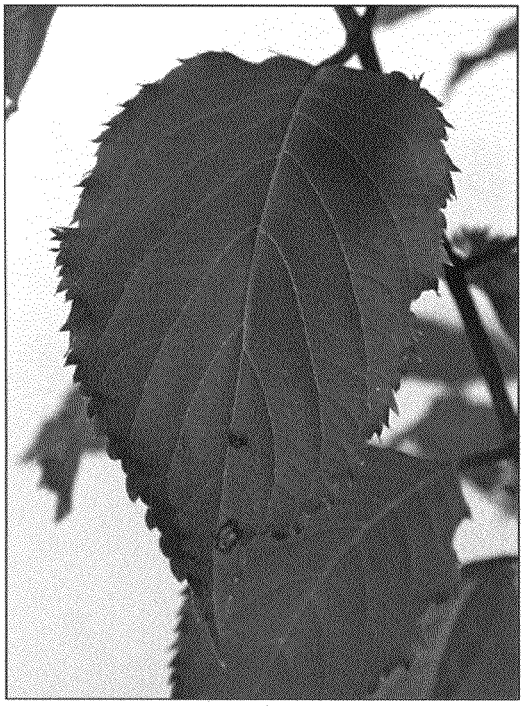

* * * * *